United States Patent
Bourque

(10) Patent No.: US 10,499,904 B2
(45) Date of Patent: Dec. 10, 2019

(54) ANCHOR INSERTION SYSTEM AND METHOD OF USE THEREOF

(71) Applicant: Smith & Nephew, Inc., Memphis, TN (US)

(72) Inventor: Bernard J. Bourque, Rehoboth, MA (US)

(73) Assignee: Smith & Nephew, Inc., Memphis, TN (US)

( * ) Notice: Subject to any disclaimer, the term of this patent is extended or adjusted under 35 U.S.C. 154(b) by 182 days.

(21) Appl. No.: 15/551,190

(22) PCT Filed: Feb. 17, 2016

(86) PCT No.: PCT/US2016/018234
§ 371 (c)(1),
(2) Date: Aug. 15, 2017

(87) PCT Pub. No.: WO2016/133996
PCT Pub. Date: Aug. 25, 2016

(65) Prior Publication Data
US 2018/0028169 A1     Feb. 1, 2018

Related U.S. Application Data

(60) Provisional application No. 62/117,243, filed on Feb. 17, 2015.

(51) Int. Cl.
*A61B 17/04* (2006.01)
*A61B 17/34* (2006.01)
(Continued)

(52) U.S. Cl.
CPC ...... *A61B 17/0401* (2013.01); *A61B 17/3468* (2013.01); *A61B 2017/00367* (2013.01);
(Continued)

(58) Field of Classification Search
CPC ............... A61B 17/04; A61B 17/0401; A61B 2017/00367; A61B 2017/3468;
(Continued)

(56) References Cited

U.S. PATENT DOCUMENTS 1,527,291 A    7/1923   Zorraquin
2,623,521 A    12/1952  Shaw
(Continued)

FOREIGN PATENT DOCUMENTS

CN    2553748 A    6/2003
CN    101730506 A  6/2010
(Continued)

OTHER PUBLICATIONS

International Preliminary Report on Patentability for related PCT Application No. PCT/US2016/018234 dated Aug. 22, 2017.
(Continued)

*Primary Examiner* — George J Ulsh
(74) *Attorney, Agent, or Firm* — Burns & Levinson, LLP; Joseph M. Maraia

(57) ABSTRACT

An arthroscopic anchor insertion tool and method for inserting consecutive, longitudinally aligned anchors from a common deployment channel of a cannulated needle by employing positive stops to prevent travel of an actuator from simultaneously advancing multiple anchors into a surgical site.

15 Claims, 9 Drawing Sheets

(51) Int. Cl.
*A61B 90/00* (2016.01)
*A61B 17/00* (2006.01)

(52) U.S. Cl.
CPC ............... *A61B 2017/0409* (2013.01); *A61B 2017/0417* (2013.01); *A61B 2090/034* (2016.02)

(58) Field of Classification Search
CPC .... A61B 2017/0409; A61B 2017/0417; A61B 2017/0464; A61B 2090/034
See application file for complete search history.

(56) References Cited

U.S. PATENT DOCUMENTS

| | | | |
|---|---|---|---|
| 5,104,381 A | 4/1992 | Gresl et al. | |
| 5,137,509 A | 8/1992 | Freitas | |
| 5,320,608 A | 6/1994 | Gerrone | |
| 5,401,247 A | 3/1995 | Yoon | |
| 5,509,910 A | 4/1996 | Lunn | |
| 5,569,288 A | 10/1996 | Yoon | |
| 5,573,511 A | 11/1996 | Yoon | |
| 5,578,053 A | 11/1996 | Yoon | |
| D379,515 S | 5/1997 | Kuehn et al. | |
| 6,001,084 A | 12/1999 | Rick et al. | |
| 6,071,292 A | 6/2000 | Makower et al. | |
| 6,270,484 B1 | 8/2001 | Yoon | |
| 6,656,160 B1 | 12/2003 | Taylor et al. | |
| 6,837,878 B2 | 1/2005 | Smutney et al. | |
| 8,202,251 B2 | 6/2012 | Bierman et al. | |
| 2002/0099335 A1 | 7/2002 | Zohmann | |
| 2003/0220677 A1 | 11/2003 | Doan et al. | |
| 2004/0133124 A1 | 7/2004 | Bates et al. | |
| 2004/0171986 A1 | 9/2004 | Tremaglio, Jr. et al. | |
| 2004/0225180 A1 | 11/2004 | Junger | |
| 2005/0159762 A1 | 7/2005 | Nuutinen | |
| 2006/0089609 A1 | 4/2006 | Bleich et al. | |
| 2008/0188928 A1 | 8/2008 | Salahieh et al. | |
| 2009/0157099 A1 | 6/2009 | Surti | |
| 2009/0163934 A1 | 6/2009 | Raschdorf et al. | |
| 2009/0275970 A1 | 11/2009 | Leibowitz | |
| 2009/0287236 A1 | 11/2009 | Bakos et al. | |
| 2009/0299400 A1 | 12/2009 | Wayman et al. | |
| 2010/0036361 A1 | 2/2010 | Nguyen et al. | |
| 2010/0113873 A1 | 5/2010 | Suzuki et al. | |
| 2010/0160731 A1 | 6/2010 | Giovannini et al. | |
| 2010/0249750 A1 | 9/2010 | Racz | |
| 2011/0022083 A1* | 1/2011 | DiMatteo ........... A61B 17/0401 606/228 |
| 2011/0082538 A1 | 4/2011 | Dahlgren et al. | |
| 2011/0218485 A1 | 9/2011 | Tran et al. | |
| 2011/0224742 A1 | 9/2011 | Weisel et al. | |
| 2011/0257581 A1 | 10/2011 | Koziczynski et al. | |
| 2013/0211427 A1 | 8/2013 | Castell | |

FOREIGN PATENT DOCUMENTS

| | | |
|---|---|---|
| EP | 2149339 A2 | 1/2010 |
| EP | 2277457 A1 | 1/2011 |
| GB | 2064963 A | 6/1981 |
| GB | 2397235 A | 7/2004 |
| JP | S56-101305 U | 8/1981 |
| JP | H08-511711 A | 12/1996 |
| JP | H09-103433 A | 4/1997 |
| JP | 2012179087 A | 9/2012 |
| JP | 2013013592 A | 1/2013 |
| SU | 1232236 A1 | 5/1986 |
| SU | 1303149 A1 | 4/1987 |
| SU | 1560143 A1 | 4/1990 |
| WO | 94/06681 A3 | 11/1994 |
| WO | 95/00189 A1 | 1/1995 |
| WO | 2001006938 A1 | 2/2001 |
| WO | 2009114833 A1 | 9/2009 |
| WO | 2012006161 A2 | 1/2012 |
| WO | 2012096816 A1 | 7/2012 |

OTHER PUBLICATIONS

Chinese Application No. 201680010793.2 Text of First Office Action.
Chinese Application No. 201680010793.2 Search Report dated Aug. 7, 2019.
International Search Report for PCT/US2016/018234 dated Jun. 3, 2016.

* cited by examiner

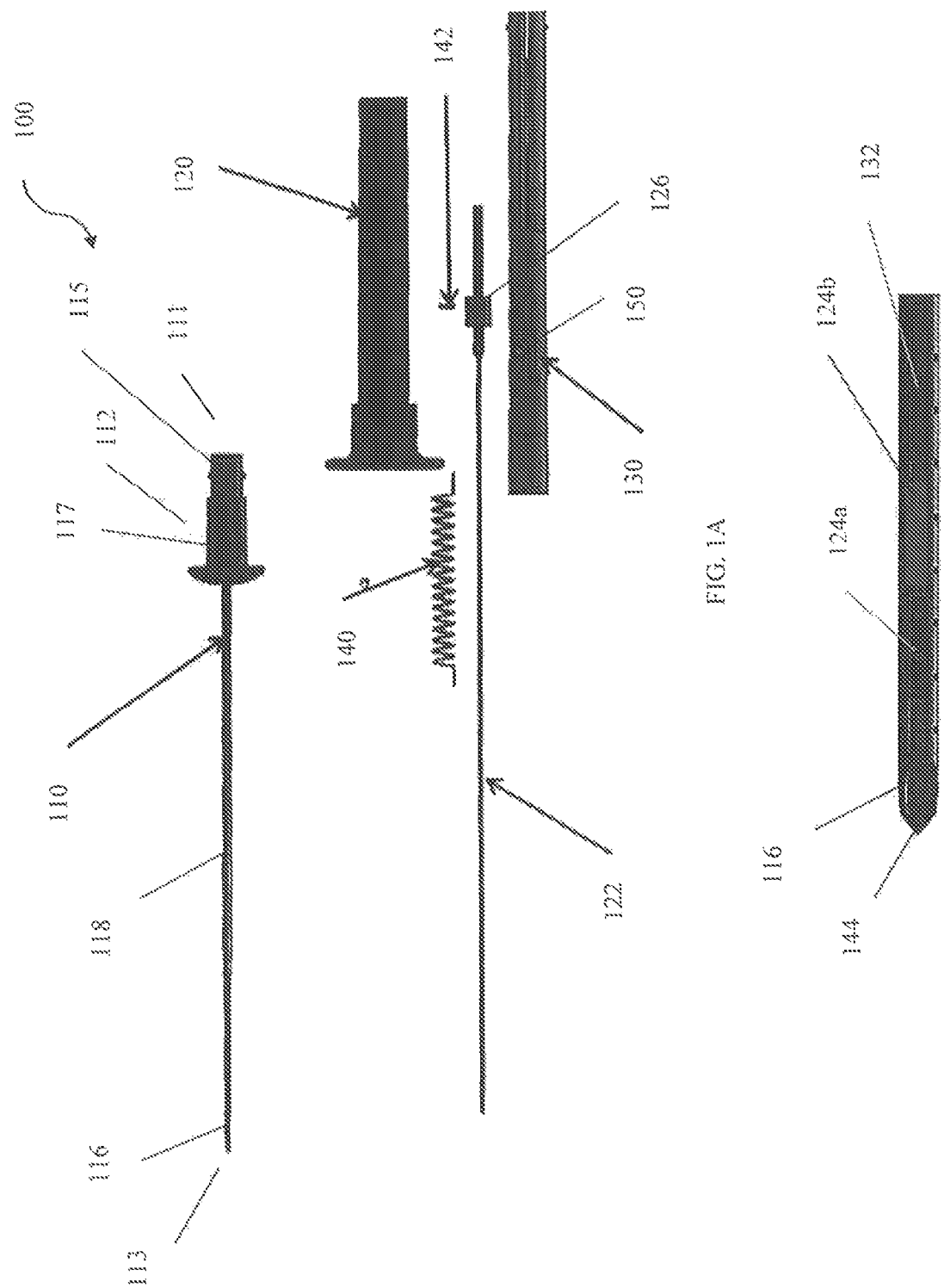

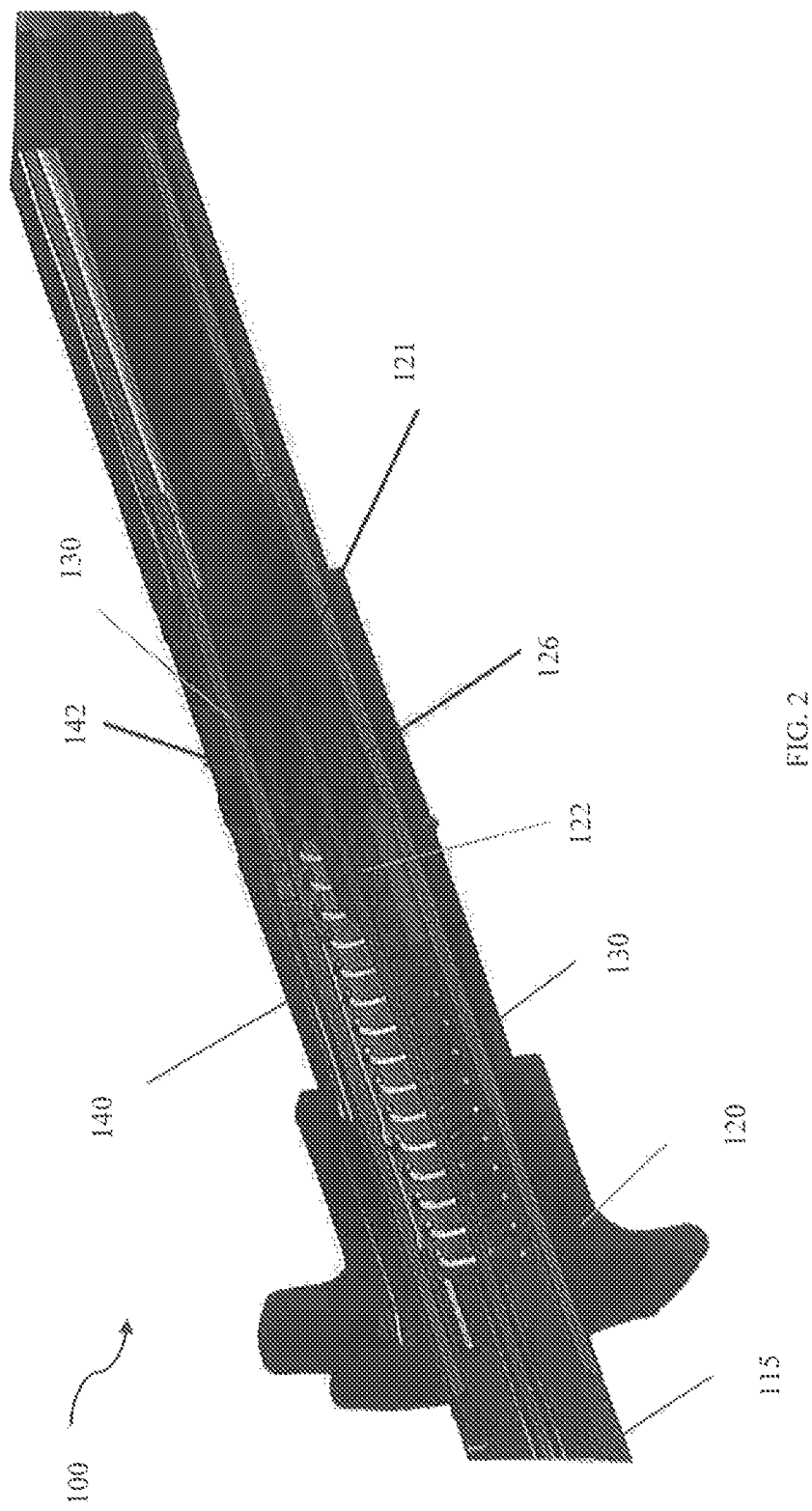

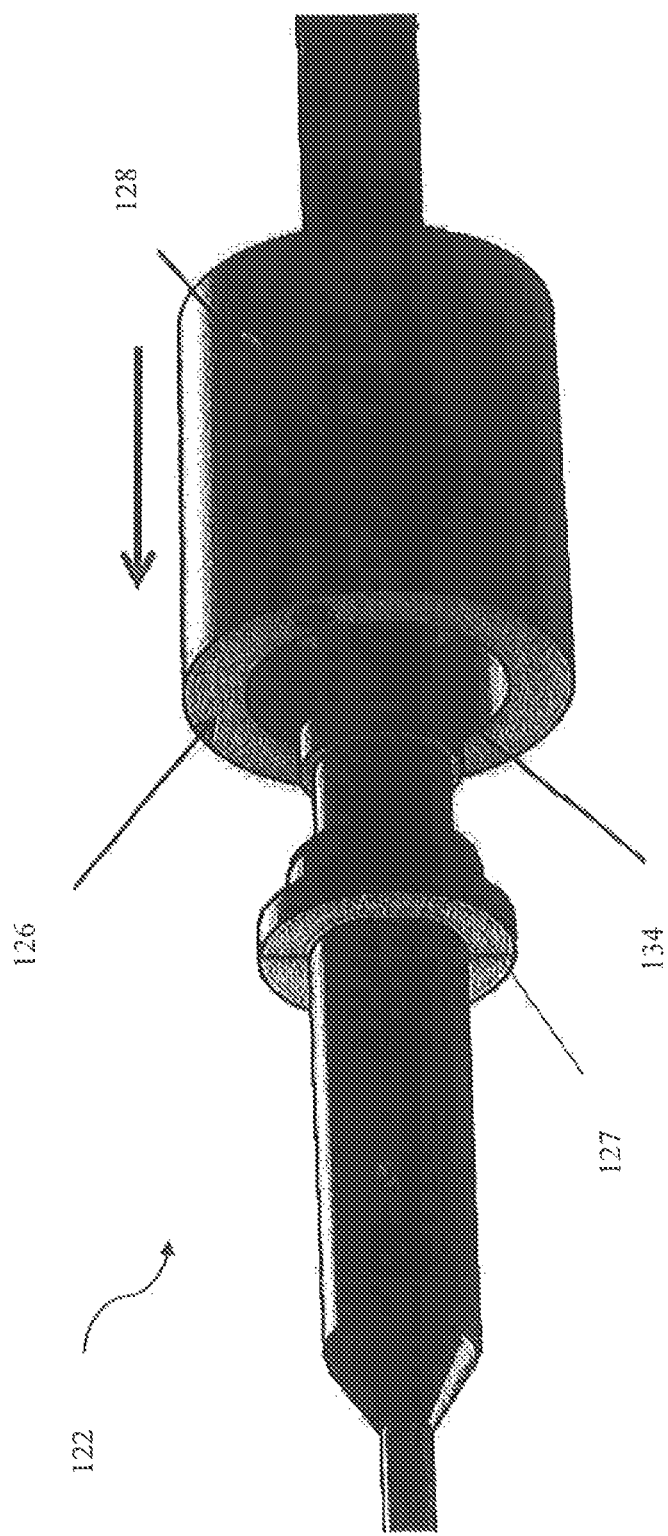

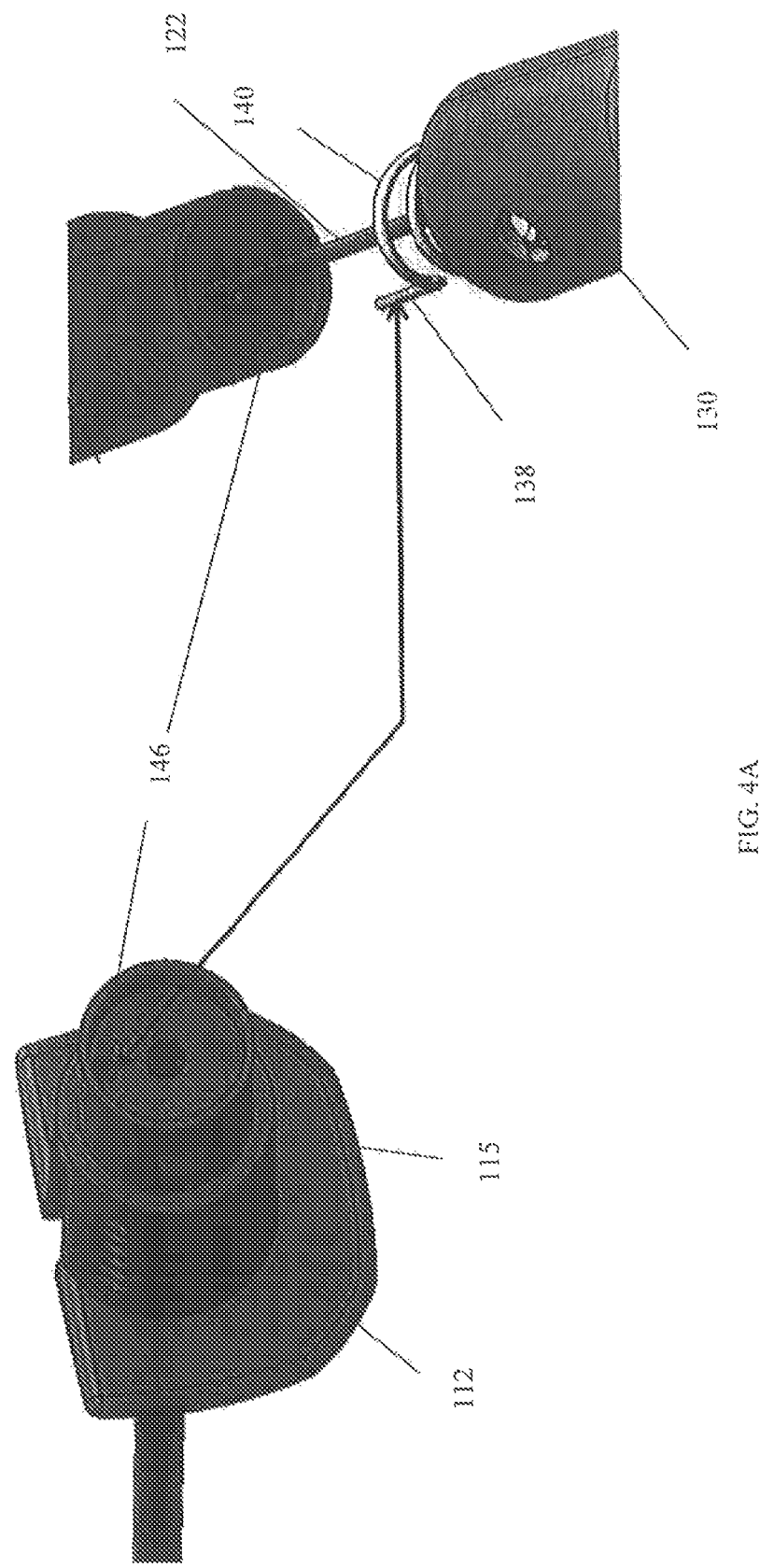

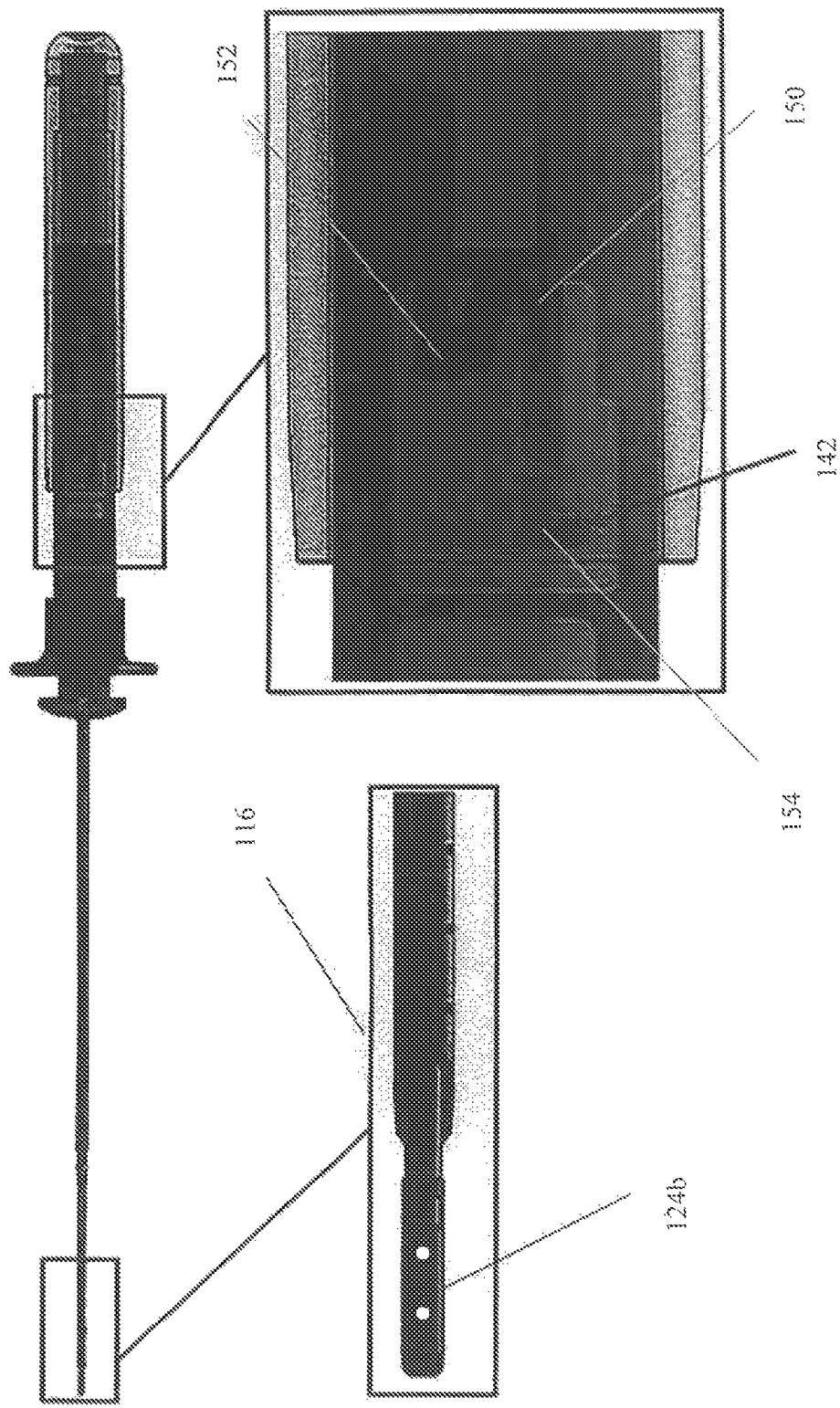

ANCHOR INSERTION SYSTEM AND METHOD OF USE THEREOF

CROSS-REFERENCE TO RELATED APPLICATIONS

This application is the U.S. national phase entry under 35 U.S.C. § 371 of International Application No. PCT/US2016/018234, filed Feb. 17, 2016, entitled ANCHOR INSERTION SYSTEM AND METHOD OF USE THEREOF, which in turn claims priority to and benefit of U.S. Provisional Application No. 62/117,243, filed Feb. 17, 2015, the contents of which are incorporated herein by reference in their entirety for all purposes.

BACKGROUND

Fibrous tissue wounds, such as muscle, ligament, and cartilage tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue. To simplify the wound closure procedure and to improve fixation, various types of suture anchors have been developed. In one example of a suture anchor, one end of a suture is fixed to a resiliently-deformable, bar-shaped suture anchor. The anchor is loaded into the bore of a hollow needle and deployed into or against the fibrous tissue. The surgeon then threads the suture across the wound and tensions a free end of the suture to pull the wound closed. When the surgeon tensions the suture, the anchor becomes oriented transversely to the suture hole, anchoring the suture in place.

More than one anchor can also be deployed using a single hollow needle, rather than two separate needles. However, an issue arises when the two anchors are placed together inside of a needle. The needle actuator may push both anchors outside of the needle simultaneously, when what is desired is to have the two anchors deploy separately. Conventional approaches require precision when disposing the actuator inside of the needle so as not to prematurely release the second anchor.

SUMMARY

Disclosed herein is an anchor insertion tool and method for inserting consecutive, longitudinally aligned anchors by employing positive stops to prevent travel of an actuator from simultaneously advancing multiple fasteners into a surgical site from a common deployment channel of a cannulated needle. Advantageously, the proposed approach prevents both over-insertion and premature deployment of the anchors.

In an example, the anchor insertion system includes a needle, the needle having a proximal end, a distal end, and a hollow shaft extending between the proximal and distal ends, the proximal end of the needle having a handle, and the distal end of the needle having a needle tip assembly for housing at least two anchors. The anchor insertion system also includes an actuator assembly for deploying at least one of the at least two anchors from the needle tip assembly, at least a portion of the actuator assembly slidably disposed within the needle. The anchor insertion system also has a cylindrical disk rotatably attached to the actuator assembly, a surface of the cylindrical disk comprising a hole for receiving a guide pin, and a sleeve disposed around the cylindrical disk, a portion of a surface of the sleeve defining an angled slot therethrough. The guide pin is configured to engage the angled slot, and the angled slot defines first and second stops for preventing the actuator assembly from simultaneously deploying the at least two anchors into a surgical site.

In other examples, the anchor insertion system further includes a deployment knob at least partially in contact with the rotary disk for advancing the actuator assembly. The at least two anchors are longitudinally aligned within a channel of the needle tip assembly. The anchor insertion system further has a spring for joining the handle to the cylindrical disk. Rotation of the handle gives the spring a torsional and/or compressional load sufficient to activate the actuator assembly. The cylindrical disk is configured to rotate both clockwise and counterclockwise 360 degrees. The at least two anchors are in an undeployed position when the guide pin is located at a proximal end of the angled slot. The first stop in the angled slot corresponds to an insertion depth of the actuator assembly for deploying a first one of the at least two anchors, and the second stop in the angled slot corresponds to an insertion depth of the actuator assembly for deploying a second one of the at least two anchors. The second stop is distal to the first stop along the surface of the sleeve. The needle tip assembly has a pointed distal end for piercing tissue. The handle includes a proximal handle portion and a distal handle portion, an outer diameter of the distal handle portion selected to be larger than an outer diameter of the proximal handle portion. An inner diameter of the sleeve is selected to slide over the proximal handle portion. When the sleeve is slid over the proximal handle portion, the sleeve and the proximal handle portion are locked into place. An outer diameter of the sleeve is selected to match the outer diameter of the distal handle portion.

An example of the method of surgical repair of this disclosure includes inserting a needle into a first location in tissue, the needle having a proximal end, a distal end, and a hollow shaft extending between the proximal and distal ends, the proximal end of the needle comprising a handle, the distal end of the needle having a needle tip assembly for housing at least two anchors; advancing an actuator assembly slidably disposed within the needle to a first position to deploy a first anchor of the at least two anchors out of the needle into the first location; retracting the actuator assembly; removing the needle from the first location in the tissue and inserting the needle into a second location in the tissue; and advancing the actuator assembly to a second position to deploy a second anchor of the at least two anchors out of the needle into the second location in the tissue, the second position being distal to the first position. In further examples, the first position and the second position are defined by a first stop and a second stop, respectively, of an angled slot, the angled slot defined by a surface of a sleeve disposed around the actuator assembly. The actuator assembly is associated with a rotary disk for housing a guide pin, the guide pin configured to contact the angled slot. The method further includes loading the at least two anchors within a channel of the needle tip assembly prior to inserting the needle into the first location in the tissue.

BRIEF DESCRIPTION OF THE DRAWINGS

The foregoing and other features will be apparent from the following description of particular embodiments disclosed herein, as illustrated in the accompanying drawings.

FIG. 1A shows an exploded view of the anchor insertion system of this disclosure;

FIG. 1B shows further detail of the needle tip assembly of FIG. 1A;

FIG. 2 shows a perspective view of the system of FIG. 1A;

FIGS. 3A-C show the guide pin in the system of FIG. 1A;

FIGS. 4A-C show the spring for biasing an actuator in the system of FIG. 1A; and FIGS. 5-7 show sectional views illustrating a method of use of the system of FIG. 1A.

DETAILED DESCRIPTION

Figure 3C:
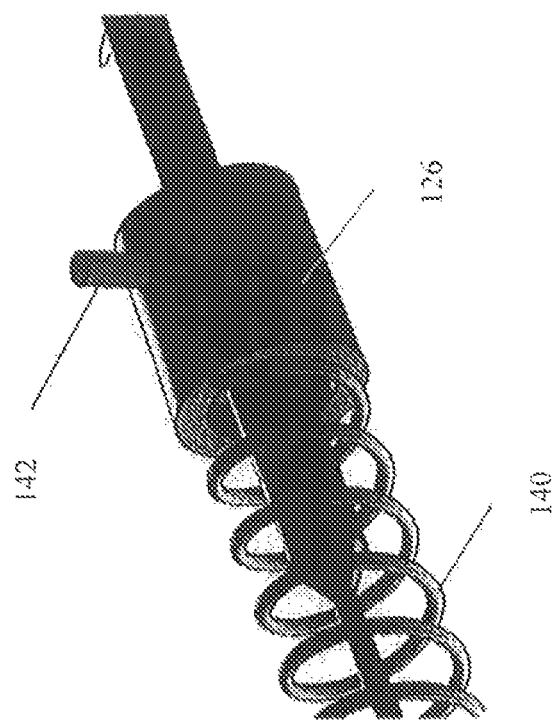

Examples of the anchor insertion system and method of use will now be discussed with reference to the figures.

In the description that follows, like components have been given the same reference numerals, regardless of whether they are shown in different examples. To illustrate an example(s) of the present invention in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

Referring now to FIG. 1A, the anchor insertion system 100 of this disclosure is shown in an exploded view. The anchor insertion system 100 includes a needle 110 having a proximal end 111 and a distal end 113, and a hollow shaft 118 extending between the proximal and distal ends 111, 113. A handle 112 is mounted to the proximal end 111 of the hollow shaft 118 and comprises a passageway therethrough (not shown) in communication with the interior of the hollow shaft 118. The handle 112 further comprises a proximal handle portion 115 and a distal handle portion 117, an outer diameter of the distal handle portion 117 being larger than an outer diameter of the proximal handle portion 115. A needle tip assembly 116 is formed at the distal end 113 of the hollow shaft 118. The hollow shaft 118 and the needle tip assembly 116 are preferably made of metal.

The anchor insertion system 100 also includes an actuator assembly 122 associated with a rotary disk 126, which may be in the form of an open cylinder. At least a portion of the actuator assembly 122 may be comprised of a flexible material, such as Nitinol. A surface of the rotary disk 126 comprises a hole for receiving a guide pin 142, as further described below. An inner diameter of a channel tube 130, which may be in the form an open sleeve, is selected to slide over the proximal handle portion 115 as well as a portion of the actuator assembly 122, such that the channel tube 130 is in contact with the guide pin 142 when the anchor insertion system 100 is assembled. The channel tube 130 may be formed from an injection molded thermoplastic or other suitable material. An outer diameter of the channel tube 130 is selected to match the outer diameter of the distal handle portion 117. A portion of the surface of the channel tube 130 defines an angled slot 150 formed therethrough. A compression spring 140 is configured for joining the rotary disk 126 and the proximal handle portion 115, as further described below. An inner diameter of a deployment knob 120 having an open distal end is selected to slide over the channel tube 130 as well as the distal handle portion 117.

As shown in FIG. 1B, the needle tip assembly 116 further comprises a pointed, tissue-piercing distal end 144. The needle tip assembly 116 is configured to house anchors, which may be two anchors 124a, 124b, within a channel 132 in communication with the interior of the hollow shaft 118. It is contemplated by this disclosure that a flexible element, such as a suture (not shown), may connect the two anchors 124a, 124b. The two anchors 124a, 124b can be made from rigid, biocompatible materials, such as polyethylene, an acetal, or polypropylene. Alternatively, the two anchors 124a, 124b can be made from resiliently deformable materials or from bioabsorbable materials. The anchors 124a, 124b are preferably unitary, injection molded pieces, but can also be manufactured by other methods. A size and shape of the two anchors 124a, 124b is selected to fit within the channel 132 of the needle tip assembly 116. A proximal end of anchor 124b may have a recess (not shown) configured to accept the distal end of the actuator assembly 122. At least a portion of the actuator assembly 122 is slidably disposed within the needle 110 such that, once the piercing distal end 144 of the needle 110 pierces tissue, advancement of the actuator assembly 122 drives the anchors 124a, 124b out of the needle tip assembly 116 into the tissue. Loading of the anchors 124a, 124b and actuator assembly 122 into the needle 110 can be performed at the time of manufacture (that is, pre-loaded), or immediately prior to surgery.

In FIG. 2, a proximal portion of the anchor insertion system 100 is shown in an assembled state. Here, the proximal handle portion 115 is shown as attached via the compression spring 140 to the rotary disk 126 secured around the actuator assembly 122. The guide pin 142 extends from the rotary disk 126 through the angled slot 150 (FIG. 1A) in the channel tube 130, as further described below. An inner portion 121 of the deployment knob 120 is configured to be disposed between a proximal portion of the channel tube 130 and a proximal portion of the actuator assembly 122, such that the inner portion 121 is in contact with the rotary disk 126. The compression spring 140 forces the rotary disk 126 to press against the inner portion 121 of the deployment knob 120, allowing the deployment knob 120 to move the actuator assembly 122 forward.

Figure 3B:
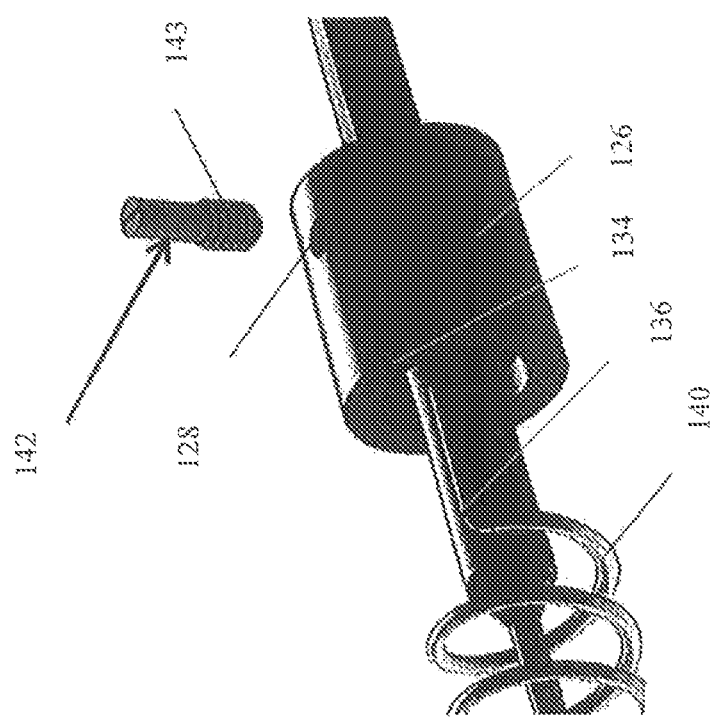

FIGS. 3A-C show detailed views of the actuator assembly 122. As shown in FIG. 3A, the rotary disk 126 is secured onto the actuator assembly 122, which may be via an interference fit with disk holder 127. The rotary disk 126 is allowed to rotate 360 degrees, both clockwise and counterclockwise. An outer surface of the rotary disk 126 includes a threaded hole 128 for receiving a threaded end 143 of the guide pin 142 (FIG. 3B). The rotary disk 126 further includes a distal hole 134 to locate and stabilize the compression spring 140. A first finger 136 at the proximal end of the compression spring 140 slides into the distal hole 134 on the rotatory disk 126 (FIG. 3C).

Figure 4C:
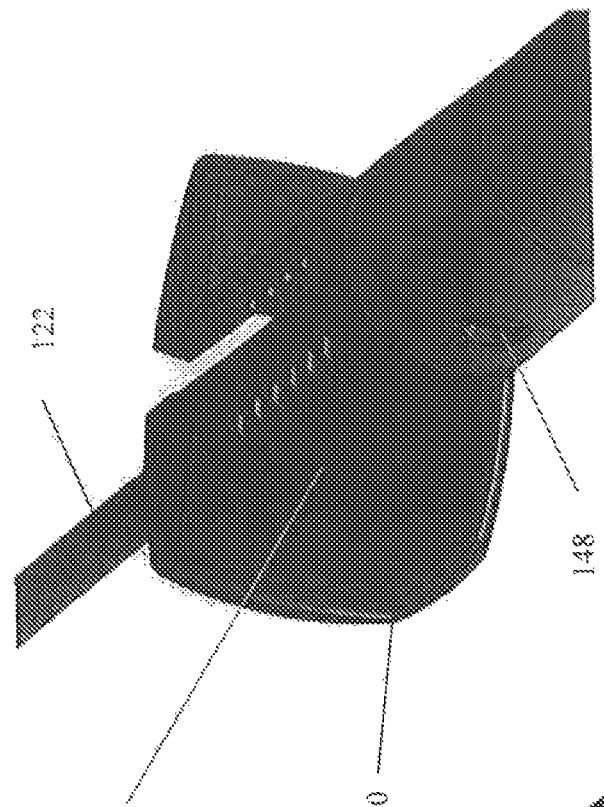
Figure 4B:
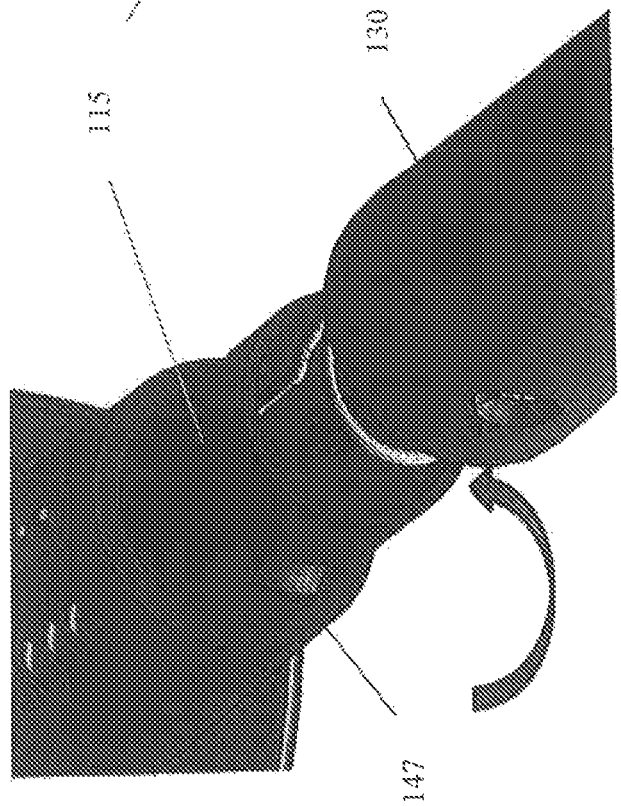

As shown in FIG. 4A, a second finger 138 at the distal end of the compression spring 140 slides into a proximal hole 146 on the proximal handle portion 115. Accordingly, rotating the handle 112 counterclockwise gives the compression spring 140 a torsional load before the proximal handle portion 115 and channel tube 130 enclosing the actuator assembly 122 are locked into place. As shown in FIGS. 4B and 4C, opposing tabs 147 on the surface of the proximal handle portion 115 are configured to snap into corresponding slots 148 on the surface of the channel tube 130. The torsional and compressional load of the compression spring 140 is sufficient to activate the actuator assembly 122.

Figure 5:
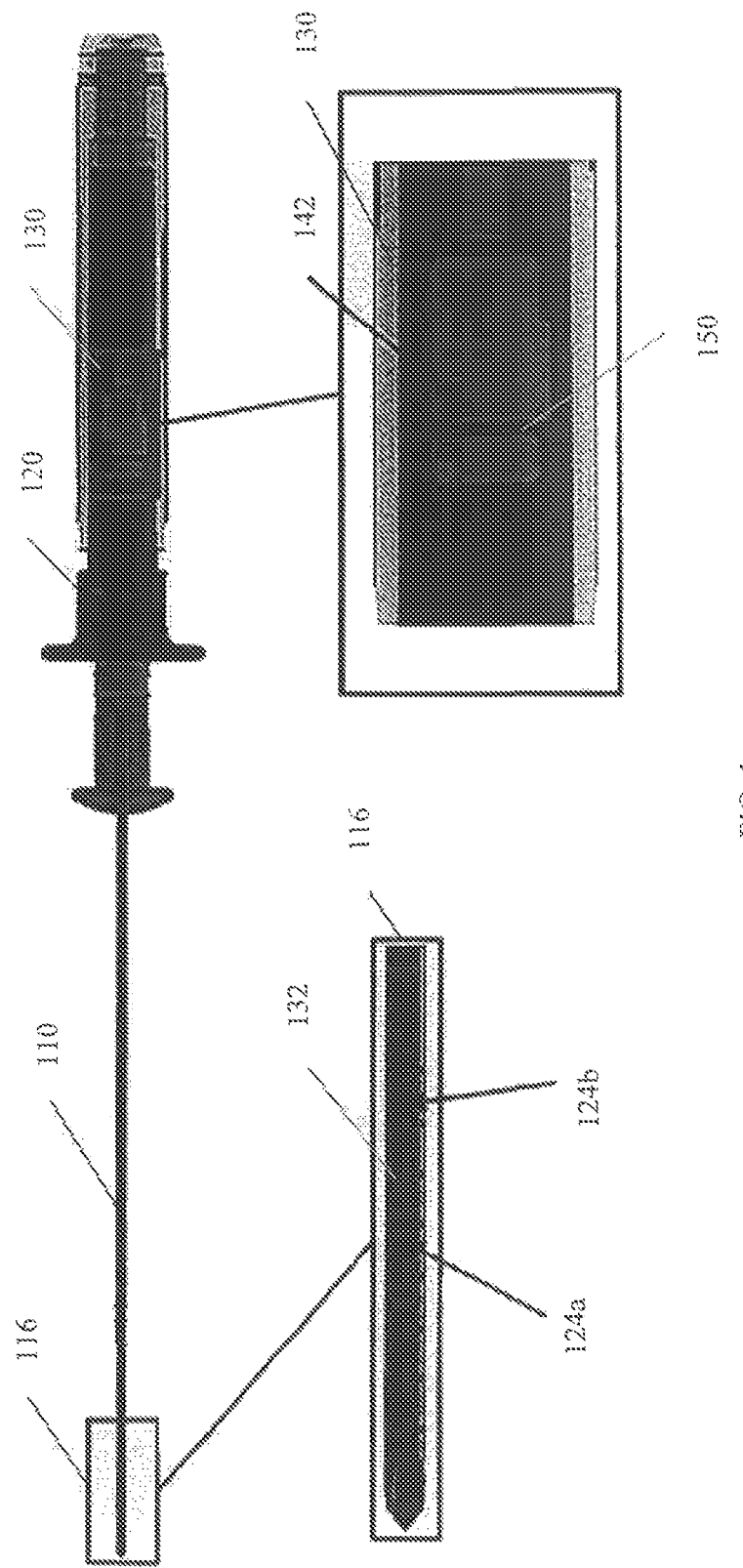
Figure 6:
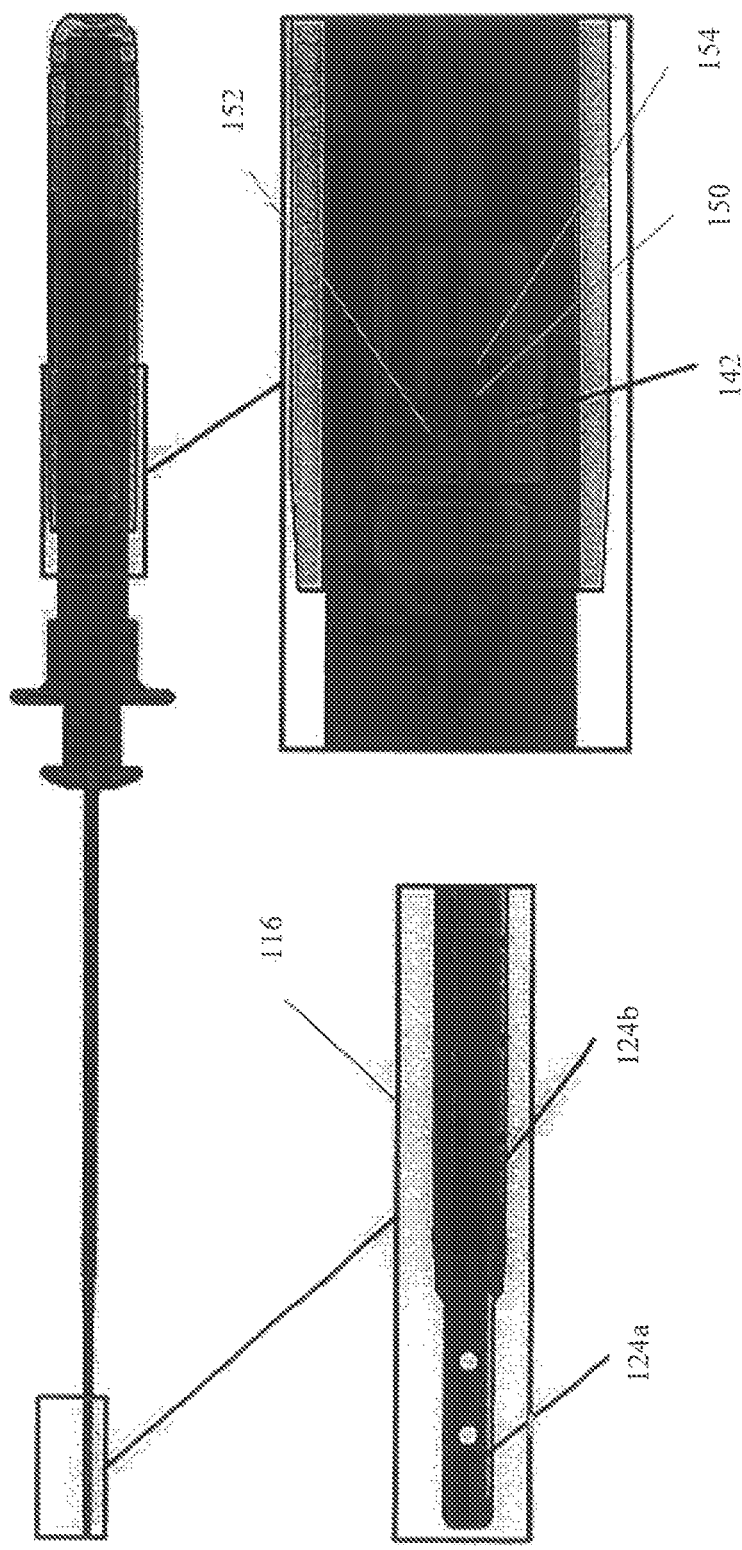

In FIGS. 5-7, sectional views of the needle tip assembly 116 and the channel guide 130 are shown. In FIG. 5, anchors 124a and 124b reside in consecutive positions in the channel 132 of the needle tip assembly 116. The guide pin 142 is shown as disposed within the angled slot 150 of the channel tube 130. The anchors 124a and 124b are in an undeployed position when the guide pin 142 is located at the proximal end of the angled slot 150. The angled slot 150 has a pattern that limits forward travel of the actuator assembly 122, as further described below.

Now turning to FIG. 6, rotation of the rotary disk 126 allows the guide pin 142 to follow the angled slot 150 axially to a 90 degree bend defining a first stop point 152. The 90 degree bend corresponds to an insertion depth of the actuator assembly 122 for deploying the first anchor 124a. The guide pin 142 stops the actuator assembly 122 which releases the first anchor 124a out of the needle tip assembly 116.

In FIG. 7, following the deployment of the first anchor 124a, the torsional force of the compression spring 140 causes rotation of the rotary disk 126 and guide pin 142 to allow slight retraction of the actuator assembly 122. The guide pin 142 moves slightly backwards from first stop point 152 along the angled slot 150, then follows the angled slot 150 forward to a portion corresponding to a second stop point 154 distal to the first stop point 152. This arrangement of stop points 152, 154 allows greater forward (insertion) travel for deploying the second anchor 124b. The guide pin 142 stops the actuator assembly 122 which releases anchor 124b out of the needle tip assembly 116.

In use, once the anchor insertion assembly 100 is inserted to the surgical site, rotation of the deployment knob 120 achieves the desired articulation angle. Anchors 124a and 124b have been loaded into the channel 132 in the needle tip assembly 116 prior to surgical insertion of the anchor insertion assembly 100. A surgeon inserts the needle tip assembly 116 through a first location in tissue to pierce a slit sufficiently large to pass the anchor 124a. The actuator assembly 122 is slid forward via the deployment knob 120 for disposing the first anchor 124a through the slit. The needle is removed from the first location and the procedure is repeated at a second location in the tissue for inserting the second anchor 124b. Therefore, the anchor insertion assembly 100 advantageously implements a multi-stage insertion depth limitation employing stop points 152, 154 at each insertion depth such that the stop points 152, 154 prevent travel of the actuator assembly 122 from advancing multiple anchors into the surgical site, as well as over-insertion of the anchors.

While the system, apparatus and methods defined herein have been particularly shown and described with references to embodiments thereof, it will be understood by those skilled in the art that various changes in form and details may be made therein without departing from the scope of the invention encompassed by the appended claims.

What is claimed is:

1. An anchor insertion system comprising:
    a needle, the needle having a proximal end, a distal end, and a hollow shaft extending between the proximal and distal ends, the proximal end of the needle comprising a handle, the distal end of the needle comprising a needle tip assembly for housing at least two anchors;
    an actuator assembly for deploying at least one of the at least two anchors from the needle tip assembly, at least a portion of the actuator assembly slidably disposed within the needle;
    a cylindrical disk rotatably attached to the actuator assembly, a surface of the cylindrical disk comprising a hole for receiving a guide pin;
    a sleeve disposed around the cylindrical disk, a portion of a surface of the sleeve defining an angled slot therethrough;
    wherein the guide pin is configured to engage the angled slot; and
    wherein the angled slot defines first and second stops for preventing the actuator assembly from simultaneously deploying the at least two anchors into a surgical site.

2. The system of claim 1, further comprising a deployment knob at least partially in contact with the cylindrical disk for advancing the actuator assembly.

3. The system of claim 1, wherein the at least two anchors are longitudinally aligned within a channel of the needle tip assembly.

4. The system of claim 1, further comprising a spring for joining the handle to the cylindrical disk.

5. The system of claim 4, wherein rotation of the handle gives the spring a torsional and/or compressional load sufficient to activate the actuator assembly.

6. The system of claim 1, wherein the cylindrical disk is configured to rotate both clockwise and counterclockwise 360 degrees.

7. The system of claim 1, wherein the at least two anchors are in an undeployed position when the guide pin is located at a proximal end of the angled slot.

8. The system of claim 1, wherein the first stop in the angled slot corresponds to an insertion depth of the actuator assembly for deploying a first one of the at least two anchors.

9. The system of claim 1, wherein the second stop in the angled slot corresponds to an insertion depth of the actuator assembly for deploying a second one of the at least two anchors.

10. The system of claim 1, wherein the second stop is distal to the first stop along the surface of the sleeve.

11. The system of claim 1, wherein the needle tip assembly comprises a pointed distal end for piercing tissue.

12. The system of claim 1, wherein the handle comprises a proximal handle portion and a distal handle portion, an outer diameter of the distal handle portion selected to be larger than an outer diameter of the proximal handle portion.

13. The system of claim 12, wherein an inner diameter of the sleeve is selected to slide over the proximal handle portion.

14. The system of claim 13, wherein, when the sleeve is slid over the proximal handle portion, the sleeve and the proximal handle portion are locked into place.

15. The system of claim 12, wherein an outer diameter of the sleeve is selected to match the outer diameter of the distal handle portion.

* * * * *